United States Patent [19]

Deftos et al.

[11] 4,438,208
[45] Mar. 20, 1984

[54] REGION-SPECIFIC DETERMINANTS FOR VITAMIN K DEPENDENT BONE PROTEIN

[75] Inventors: Leonard J. Deftos, Del Mar; Bayard D. Catherwood, San Diego, both of Calif.

[73] Assignee: The Regents of the University of California, Berkeley, Calif.

[21] Appl. No.: 382,844

[22] Filed: May 27, 1982

[51] Int. Cl.$^3$ .................... G01N 33/54; G01N 33/56; G01N 33/58; C07C 103/52
[52] U.S. Cl. .................. 436/542; 436/543; 436/544; 436/545; 436/547; 260/112.5 R
[58] Field of Search ............ 424/1.1, 5; 436/542, 436/543, 544, 545, 547; 266/112.5 R

[56] References Cited

U.S. PATENT DOCUMENTS 3,852,157  12/1974  Rubenstein et al. ............ 424/12 X
3,966,556   6/1976  Rubenstein et al. ............ 424/7

OTHER PUBLICATIONS

Poser et al., J. Biol. Chem.: 255(18): 8685–91, (1980).
Price et al., Proc. Natl. Acad. Sci. U.S.A.:77(4) 2234–38 (1980).
Lian et al., Fed. Proc.: 37(12) 2615–20, (1978).
Hauschka et al., Proc. Natl. Acad. Sci. U.S.A.: 72(10) 3925–29, (1975).
Price et al., J. Biol. Chem.: vol. 256, (3) 1172–6 (1981).
Price et al., J. Clin. Inves.: 66(5) 878–83, (1980).
Nishimoto, Diss. Abstracts Int.: 41(7) 2448B, (1981).
Price et al., J. Biol. Chem.: 256(8) 3781–84, (1981).
Price et al., Biochem. Biophys. Res. Comm. 99(3) 928–35, (1981).

*Primary Examiner*—Christine M. Nucker
*Attorney, Agent, or Firm*—Bertram I. Rowland

[57] ABSTRACT

Novel oligopeptide used as reagents or in the preparation of reagents in relation to gamma-carboxyglutamic acid-containing protein of bone. Particularly, labeled oligopeptides and antibodies prepared from immunogen conjugates are disclosed for use in immunoassays.

18 Claims, No Drawings

REGION-SPECIFIC DETERMINANTS FOR VITAMIN K DEPENDENT BONE PROTEIN

This invention was made with Government support under Grant No. AM15888 awarded by the Department of Health and Human Services. The Government has certain rights in this invention.

BACKGROUND OF THE INVENTION

1. Field of the Invention

As increasing knowledge is obtained concerning vitamin K dependent bone protein, referred to hereinafter as bone Gla protein (BGP) or γ-carboxyglutamic acid containing protein, assays will be required having an enhanced sensitivity and specificity. That is, where antibodies are employed, it will be necessary that the antibodies be specific for the protein of interest and in particular defined regions of protein, having substantially different binding affinities between the protein of interest and regions thereof, and other proteins. The greater the binding affinity, all other things being equal, the greater the sensitivity of the assay.

2. Description of the Prior Art

An abstract of a paper by Price, et al., was published in June, 1979, for the meeting of the American Society for Bone and Mineral Research. Price and Nishimoto, *Proc. Natl. Acad. Sci.* USA 77: 2234-2238 (1980) and Price, et al., *J. Clin. Invest.* 66: 878-883 (1980) both describe a radioimmunoassay utilizing antibodies and labels derived from the intact BGP molecule. Deftos, et al., *Calcif. Tissue Int.*, 34: 121-124 (1982) describes the clinical measurement of changes in BGP during treatment of bone disease. The references cited in the aforementioned references should also be noted. Copending application Ser. No. 246,972 suggests the use of fragments of BGP of at least 20 amino acids as reagents in immunoassays for BGP.

SUMMARY OF THE INVENTION

Small oligopeptides are provided capable of being employed as haptens for the preparation of highly specific antibodies for BGP. Particularly, the oligopeptides are of from about 10 to 16 amino acids and have the same or substantially the same amino acid sequence as the naturally occurring BGP. These are employed for the preparation of antibodies, and for use as labelled reagents in sensitive immunoassays.

DESCRIPTION OF THE SPECIFIC EMBODIMENTS

Novel oligopeptides are provided for use as reagents for and the preparation of reagents for the detection of bone Gla protein (BGP, previously described as vitamin K dependent protein) in physiological fluid, particularly blood.

High blood levels of BGP can indicate disease characterized by high bone turnover. It is therefore important to be able to detect BGP in a quantitative manner, so as to be able to detect the amount of BGP in the blood and the changes in concentration of BGP over time, particularly before and after treatment for bone disease.

The compounds of this invention are oligopeptides which have the same or substantially the same amino acid sequence as regions of BGP. By having oligopeptides which mimic only a portion of the BGP, antibodies can be obtained which are highly specific for BGP and regions thereof, minimizing cross-reactivity and providing for high binding titer.

For purposes of reference, the structure of human BGP (hBGP) is set forth, since the oligopeptides will refer to fragments of this molecule. The following is the amino acid sequence of hBGP.

$$\overset{5}{\phantom{X}}\qquad\overset{10}{\phantom{X}}\qquad\overset{15}{\phantom{X}}$$
TyrLeuTyrGlnTrpLeuGlyAlaProValProTyrProAspPro $$\overset{20}{\phantom{X}}\qquad\overset{25}{\phantom{X}}\qquad\overset{30}{\phantom{X}}$$
LeuGluProArgArgGlaValCysGlaLeuAsnProAspCysAsp $$\overset{35}{\phantom{X}}\qquad\overset{40}{\phantom{X}}\qquad\overset{45}{\phantom{X}}$$
GluLeuAlaAspHisIleGlyPheGlnGluAlaTyrArgArgPhe $$\overset{49}{\phantom{X}}$$
TyrGlyProVal For the most part, the oligopeptides which find use will be from 10 to 16 amino acids, more usually from 10 to 15 amino acids, and preferably from about 12 to 15 amino acids. The sequences will usually come within the amino acid fragments 1-15; 15-30; and 35-49, although in certain cases it will be desirable to use oligopeptides which span these fragments.

For the most part, the oligopeptides will have the identical amino acid sequence of the hBGP, but in particular situations, one or more amino acids may be substituted. For example, the aromatic amino acids may be changed, that is, a tyrosine may be substituted by phenylalanine or the reverse. Also, glutamic acid may be substituted for γ-carboxyglutamic acid. One amino acid may be replaced by a different amino acid to improve the properties of the oligopeptide. For example, tyrosine may be replaced by phenylalanine to reduce oxidation susceptibility or the reverse substitution to facilitate hapten conjugation with a particular linking group, particularly one having a active azo functionality.

Of particular interest are the five oligopeptides hBGP$^{1-11\ or\ 12}$; hBGP$^{15\ or\ 16-30}$ and hBGP$^{37-49}$, the last oligopeptide being of particular interest.

The oligopeptides of this invention may be made in a variety of ways, such as synthetic, using the Merrifield technique, manually or with a commercially available apparatus. The manner in which the oligopeptides are prepared is not critical to this invention and any convenient method may be employed.

Depending upon the purpose of the oligopeptide, up to 4 amino acids may be changed, usually not more than 3, but not more than 1 change other than a phenylalanine to a tyrosine or vice versa, or glutamic acid for γ-carboxyglutamic acid. Two similarly structured aromatic amino acids may be exchanged, and in some instances, the substitution may involve a totally different amino acid. Illustrative modifications include (Tyr$^{15}$) hBGP$^{15-30}$, (Phe$^{1,3}$) hBGP$^{1-12}$, and (Tyr$^{37}$,Phe$^{42,46}$) hBGP$^{37-49}$, and (Tyr$^{15}$,Glu$^{21,24}$) hBGP$^{15-30}$.

Because the oligopeptides of this invention are much smaller than the naturally occurring protein, they can be readily synthesized by synthetic techniques. Thus, much higher yields of product can be otained, which product may then be used as haptens in the development of methods for determining BGP in physiological fluids. Furthermore, one or more amino acids in the chain may be substituted, where the desired epitopic site specificity is retained while the oligopeptide is provided with improved properties, such as stability, ease of conjugation, reduction in cross-reactivity, and the like.

The oligopeptides of this invention find use as haptens. The hapten may be conjugated to an immunogen to provide a conjugate for the production of antibodies; or the hapten may be labelled with an appropriate label which allows for detection of the distribution of the hapten in an assay for BGP.

In preparing the immunogen conjugate, a wide variety of techniques may be employed. In view of the available amino groups on both the immunogen and the oligopeptide, difunctional reagents may be used such as glutaraldehyde. Alternatively, more specific linking groups may be employed such as carboxybenzenediazosulphonate, paramaleimidobenzoic acid, or other conventional linking groups.

The particular manner in which the oligopeptide is conjugated to the immunogen as well as the particular immunogen is not critical to this invention. Various conventional immunogens may be used, which immunogens will depend upon the particular host which is injected. Common immunogens include bovine serum albumin, bovine gammagloblin, rabbit serum albumin, keyhole limpet hemocyanin, etc.

Depending upon whether polyclonal or monoclonal antibodies are desired, different hosts will be injected. For preparation of monoclonal antibodies, see particularly U.S. Pat. Nos. 4,196,265 and 4,172,124; Kohler and Milstein Nature (1975), 365: 495–497; and Kennett (ed.), "Monoclonal Antibodies-Hybridomas: A New Dimension in Biological Analyses, Plenum Press, N.Y., 1980.

In conjunction with the antibodies, labelled hapten is employed for the immunoassays. A wide variety of labels may be used as radionuclides, enzymes, fluorescers, magnetic particles, stable free radicals, chemiluminescers, etc. Illustrative labels include $^{125}I$, $^3H$, fluorescein, dansyl, rhodamines, acridines, horse radish peroxidase, amylase, lysozyme, glucose-6-phosphate dehydrogenase, beta-galactosidase, etc. Methods employing these various labels may be found in U.S. Pat. Nos. Re 29,169; Re 29,955; 3,654,090; 3,690,834; 3,817,837; 3,867,517; 3,935,074; 3,975,511; 3,996,345; and 4,020,151. These references are only illustrative of the wide variety of immunoassays which have been reported in the patent literature.

The manner of conjugation to the various labels will depend on the nature of the particular label. In some instances, the label will be monofunctional so that either the oligopeptide or the label may be activated to react with the other. In other instances, the label will be polyfunctional e.g. enzymes, so that it will be more convenient to activate the oligopeptide. In many of these instances, it may be desirable to use specialized reagents as previously described. For radionucide linking, tyrosines may be labelled, using an iodinating agent, such as a source of radioactive iodide and lactoperoxidase.

The assays will be carried out in accordance with know techniques depending upon the nature of the label. Various techniques involve competition between the labelled oligopeptide and the BGP analyte for binding to anti-BGP in a sample where BGP is to be measured. Various physiological fluids of interest in which BGP may be assayed include serum, plasma, urine, cerebrospinal fluid, aminotic fluid and saliva. In addition to the aforementioned biological fluids, extracts, particularly acid extracts of human tissues, such as bone, teeth and pathological calcifications (ectopic calcifications and hardened arteries) may also be of interest.

In performing the assay, the sample containing the analyte, the labelled oligopeptide and antibodies to the oligopeptide (anti-oligopeptide) will be brought together in an aqueous buffered medium, normally at a pH in the range of about 6 to 9, and the partitioning of the labelled oligopeptide between the antibody and the assay medium determined.

Depending upon the nature of the assay, the protocol and reagents, a separation ("heterogeneous") or no separation ("homogeneous") step may be involved. The difference will depend upon whether the binding of antibody to the labelled reagent affects the signal resulting from the reagent. For example, radionuclides require separation between bound and unbound label, while fluorescer labels may or may not require a separation step.

In carrying out the assay, the order of addition of the compounds may vary. All the materials may be brought together simultaneously or the sample may first be combined with the anti-oligopeptide, followed by the addition of the labelled oligopeptide. Incubation steps may be involved between the various addition, usually being not less than five minutes nor more than about 7 days. Either a rate or equilibrium measurement may be involved.

After the sample and reagents are combined, the anti-oligopeptide bound labelled oligopeptide may then the separated from the unbound labelled oligopeptide where a heterogeneous assay is involved and the signal measured from the label in accordance with the nature of the label. Where no separation is required, the signal will be determined directly from the assay medium. Depending on the nature of the radiation to be measured, gamma counters, scintillation counters, spectrophotometers, fluorometers or the like may be employed.

The following examples are offered by way of illustration and not by way of limitation.

EXPERIMENTAL

1. Preparation of the Oligopeptide

The 13 amino acid oligopeptide of the present invention was synthesized using the solid phase technique described in Barany and Merrifield, Solid-phase Peptide Synthesis, in "The Peptides, Analysis, Synthesis, Biology." Special Methods in Peptide Synthesis, Part A, Vol. 2, Gross and Merenhofer, eds. Academic Press, New York, 1980 pp 1–284.

2. Preparation of Antibodies to the Oligopeptide

Oligopeptide hBGP$^{37-49}$ (1.5 mg) was conjugated to keyhole limpet hemocyanin (1.8 mg) in phosphate-buffered saline using two additions of 1-ethyl dimethylaminopropyl carbodiimide (250 µg) at room temperature. After 24 hours, the material was dialyzed against water. Rabbits were immunized by monthly multiple site intradermal injection of the purified immunogen (50 µg) in incomplete Freund's adjuvant. Antibodies were obtained from blood samples taken from the central ear artery.

3. Preparation of Radiolabeled Oligopeptide

Oligopeptide hBGP$^{37-49}$ (0.5 µg) was iodinated in 0.05 M phosphate buffer using NaI (1 mCi $^{125}I$) by lactoperoxidase (2 µg) in the presence of β-D-glucose (2 µmoles) and glucose oxidase (0.64 ng; 125 U/mg). After 15 minutes at room temperature the mixture is diluted to a total volume of 1 ml and co-precipitated with cytochrome C (100 μg) in trichloroacetic acid (6% by weight) and phosphotungstic acid (0.25% by weight). The pellet is washed, redissolved by neutralization with 0.5 M sodium hydroxide (10–20 μl) and the tungstate is complexed by coordination with one volume of 0.5 M diethylenetriamine. The overall specific activity of the labeled peptide is greater than 500Ci/mmole. The solution is diluted to 0.5 ml with 25 mM ethanolamine-HCl (pH, 9.0) and purified by affinity chromatography on a column (0.5×20 cm) packed with PBE94 (Pharmacia, Piscataway, New Jersey) by eluting isocratically with 25 mM ethanolamine-HCl (pH 9.0) containing 10 μg/ml cytochrome C. The material obtained in peaks 3 and 4 was used in the radioimmunoassay.

4. Preparation of Calf BGP

BGP was purified from the proteins released by the mineralization of calf bone by gel filtration over Sephadex®G-100 (Pharmacia) and subsequent gradient elution from DEAE-Sephadex®A-25 (Pharmacia) as described by Price, et al., PNAS USA (1976), 73: 1447–1451. Calf BGP has the same amino acid sequence as hBGP for amino acids 37–49.

5. Preparation of Radioiodinated Calf BGP

Purified calf BGP was labeled with $^{125}I$ ($4 \times 10^{18}$ cpm/mole, Amersham) by the solid state lactoperoxidase method by incubating 10 mg of BGP with 1 mCi of $^{125}I$ (David and Rersfeld, Biochemistry, 13: 1014–1021). The labeled BGP was separated from unbound $^{125}I$ by gel filtration on a Sephadex®G-25 (Pharmacia) column equilibrated with assay diluent (0.14 M NaCl; 0.01 M phosphate; 25 mM EDTA; 0.1% gelatin; 0.1% Tween®-20 (Sigma Chemical Co., St. Louis, Missouri) at pH 7.4).

A number of assays were carried out employing the hBGP$^{37-49}$ radioiodinated reagent with the antibodies prepared as described in Example 2. The assays were performed in 0.25% bovine serum albumin, 20 mM phosphate, 1 mM EDTA with standards of hBGP$^{37-49}$ plug BGP-deficient plasma. After incubation for three days before and one day after addition of tracer, bound tracer is separated from free tracer by employing a second antibody to the rabbit antiBGP antibody. The assay detects 9 femtomoles hBGP$^{37-49}$ and shows 50% inhibition of binding at 49 femtomoles. Pure bovine BGP gave 50% of the reactivity of hBGP$^{37-49}$ on a molar basis and extracts of human bone showed high concentrations of BGP (100–300 nmol hBGP$^{37-49}$/g). Hyperparathyroid plasma showed inhibition of binding parallel to the hBGP$^{37-49}$ standard. Twenty female and twenty male normal plasma samples assayed in four assays gave an intra-assay C.V. of 17% and mean plasma hBGP levels (picomoles hBGP$^{37-49}$ ml) of 5.8±0.9 in females and 7.1±1.3 in males. The upper limit of normal is 20 pmols/ml (N=103). hBGP was elevated in 16/27 patients with hyperparathyroidism, 24/33 with Paget's disease and 12/15 with chronic renal failure on hemodialysis.

On BioGel P-30 in 1 mM MgCl$_2$, 150 mM NaCl plasma hBGP coelutes with hBGP from bone, but 20% is noncovalently bound to large plasma proteins. It is concluded that the hBGP detected by this region-specific RIA in the blood of normal human subjects is similar to the peptide in bone and is in part noncovalently bound to larger proteins.

The subject assay provides for an extremely sensitive technique for the determination of BGP in physiological fluids. Thus, patients suspected of having a variety of diseases associated with bone, can be sensitively monitored, specifically detecting variations in BGP in plasma or other fluids. Because the oligopeptides which are used are substantially smaller than the naturally occurring protein, they can be readily synthesized by convenient techniques. In addition, modifications can be made to enhance physical properties of the oligopeptides without significant loss of specificity.

Although the foregoing invention has been described in some detail by way of illustration and example for purposes of clarity of understanding, it will be obvious that certain changes and modifications may be practiced within the scope of appended claims.

We claim:

1. An oligopeptide capable of competing with hBGP for an antibody specific for hBGP which comprises:
an amino acid sequence of from 10 to 16 amino acids, wherein terminal sequences of said oligopeptide include the terminal amino acids of hBGP and up to three amino acids can be substituted with different amino acids, except that not more than one amino acid substitution can involve an exchange other than Phe and Tyr or Glu and Gla.

2. An oligopeptide capable of competing with hBGP for an antibody specific for hBGP which comprises:
an amino acid sequence of from 10 to 16 amino acids having a sequence coming within hBGP$^{1-15}$, hBGP$^{15-30}$, hBGP$^{35-49}$, wherein terminal sequences of said oligopeptide include the terminal amino acids of hBGP and up to three amino acids can be substituted with different amino acids, except that not more than one amino acid substitution can involve an exchange other than Phe and Tyr or Glu and Gla.

3. An oligopeptide according to claim 2, wherein said oligopeptide is hBGP$^{37-49}$.

4. An oligopeptide according to claim 2, wherein said oligopeptide is hBGP$^{15}$ $^{or}$ $^{16-30}$.

5. An oligopeptide according to claim 2 which oligopeptide is hBGP$^{1-11}$ $^{or}$ $^{12}$.

6. A conjugate of an oligopeptide according to any of claims 1, 2, 3, 4, or 5 wherein said oligopeptide is conjugated to a label capable of providing a detectable signal useful in a diagnostic assay for hBGP.

7. A conjugate according to claim 6, wherein said label is a radionuclide.

8. A conjugate according to claim 7, wherein in said radionuclide is radioactive iodine.

9. A conjugate according to claim 6, wherein said label is a fluorescer.

10. A conjugate according to claim 6, where in said label is an enzyme.

11. An immunogen conjugate comprising an oligopeptide according to claims 1 or 2 covalently conjugated to an immunogen.

12. An immunogen conjugate according to claim 10, wherein said immunogen is keyhole limpet hemocyanin.

13. Antibodies prepared by immunizing a host with an immunogen conjugate according to claim 11.

14. Antibodies according to claim 13, wherein said oligopeptide is hBGP$^{37-49}$.

15. A method for determining hBGP in a physiological fluid, said method employing at least one reagent selected from the group consisting of antibodies characterized by:

being obtained by immunizing a host with an immunogen conjugate of an oligopeptide capable of competing with hBGP for an antibody specific for hBGP, which oligopeptide comprises:

an amino acid sequence of from 10 to 16 amino acids having a sequence coming within hBGP$^{1-15}$, hBGP$^{15-30}$, hBGP$^{35-49}$, wherein terminal sequences of said oligopeptide include the terminal amino acids of said hBGP and up to three amino acids can be substituted with different amino acids, except that not more than one amino acid substitution can involve an exchange other than Phe and Tyr or Glu and Gla, wherein said oligopeptide is covalently conjugated to an immunogen; and labeled conjugates according to claim 6;

said method comprising:

combining in an assay medium antibodies specific for hBGP, a labeled conjugate capable of competing with hBGP for said antibodies, wherein said label provides a detectable signal; and determining the amount of labeled conjugate which is bound to said antibodies or unbound as a measure of BGP in said sample.

16. A method according to claim 15, wherein said antibodies were produced with a conjugate of hBGP$^{37-49}$ and said labeled conjugate is a radioiodinated hBGP$^{37-49}$.

17. Antibodies prepared in response to an oligopeptide according to any of claims 1 or 2.

18. Antibodies according to claim 17, wherein said antibodies are monoclonal.

* * * * *